United States Patent
Kagawa et al.

(10) Patent No.: US 9,237,840 B2
(45) Date of Patent: Jan. 19, 2016

(54) LIGHT SOURCE SYSTEM

(71) Applicant: OLYMPUS MEDICAL SYSTEMS CORP., Tokyo (JP)

(72) Inventors: Ryohei Kagawa, Hachioji (JP); Hidetsugu Takahashi, Hachioji (JP); Hidetaro Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/601,381

(22) Filed: Jan. 21, 2015

(65) Prior Publication Data

US 2015/0141758 A1 May 21, 2015

Related U.S. Application Data

(63) Continuation of application No. PCT/JP2013/064049, filed on May 21, 2013.

(30) Foreign Application Priority Data

Sep. 4, 2012 (JP) ................................ 2012-194428

(51) Int. Cl.
*A61B 1/06* (2006.01)
*A61B 1/00* (2006.01)
(Continued)

(52) U.S. Cl.
CPC ........... *A61B 1/0661* (2013.01); *A61B 1/00006* (2013.01); *A61B 1/00059* (2013.01);
(Continued)

(58) Field of Classification Search
CPC ............. A61B 1/0061; A61B 1/00006; A61B 1/0059; A61B 1/0684; A61B 1/0676
See application file for complete search history.

(56) References Cited

U.S. PATENT DOCUMENTS

2007/0100202 A1* 5/2007 Murata .............. A61B 1/00059 600/109
2008/0158348 A1* 7/2008 Karpen .............. A61B 1/00036 348/82

(Continued)

FOREIGN PATENT DOCUMENTS

JP 09-196991 A 7/1997
JP 2005-349189 A 12/2005

(Continued)

OTHER PUBLICATIONS

International Search Report dated Aug. 27, 2013 issued in PCT/JP2013/064049.

(Continued)

*Primary Examiner* — John P Leubecker
(74) *Attorney, Agent, or Firm* — Scully, Scott, Murphy & Presser, P.C.

(57) ABSTRACT

A light source system includes an endoscope having an illumination section and an illumination control section connected to the endoscope and provided with a drive circuit that generates drive pulses for driving the light source, the light source system including: a type information generating section that generates type information regarding the endoscope; a signal generating section generates a signal indicative of a duty ratio of the drive pulses which is permitted to the illumination section; a light adjusting section that outputs light-adjusted drive pulses having a duty ratio not greater than a permissible duty ratio based on the type information and a limiting section that limits the light-adjusted drive pulses to have a duty ratio not greater than a duty ratio based on the signal from the signal generating section, and provides limited pulses to the drive circuit.

15 Claims, 8 Drawing Sheets

(51) Int. Cl.
*A61B 1/04* (2006.01)
*H05B 33/08* (2006.01)

(52) U.S. Cl.
CPC .............. *A61B 1/04* (2013.01); *A61B 1/0676* (2013.01); *A61B 1/0684* (2013.01); *H05B 33/0818* (2013.01); *A61B 1/00055* (2013.01)

(56) References Cited

U.S. PATENT DOCUMENTS

| | | | | |
|---|---|---|---|---|
| 2008/0232131 A1* | 9/2008 | Suda | ............... | A61B 1/0684 362/574 |
| 2012/0123213 A1* | 5/2012 | Seto | ............... | A61B 1/0638 600/178 |
| 2014/0221740 A1* | 8/2014 | Kawula | ............. | A61B 1/00016 600/109 |

FOREIGN PATENT DOCUMENTS

| | | |
|---|---|---|
| JP | 2007-252516 A | 10/2007 |
| JP | 2009-213742 A | 9/2009 |
| JP | 2010-250114 A | 11/2010 |

OTHER PUBLICATIONS

Japanese Office Action dated May 13, 2014 issued in JP 2014-509962.

* cited by examiner (a) LED CURRENT (b) LED VOLTAGE (c) BINARIZED WAVEFORM

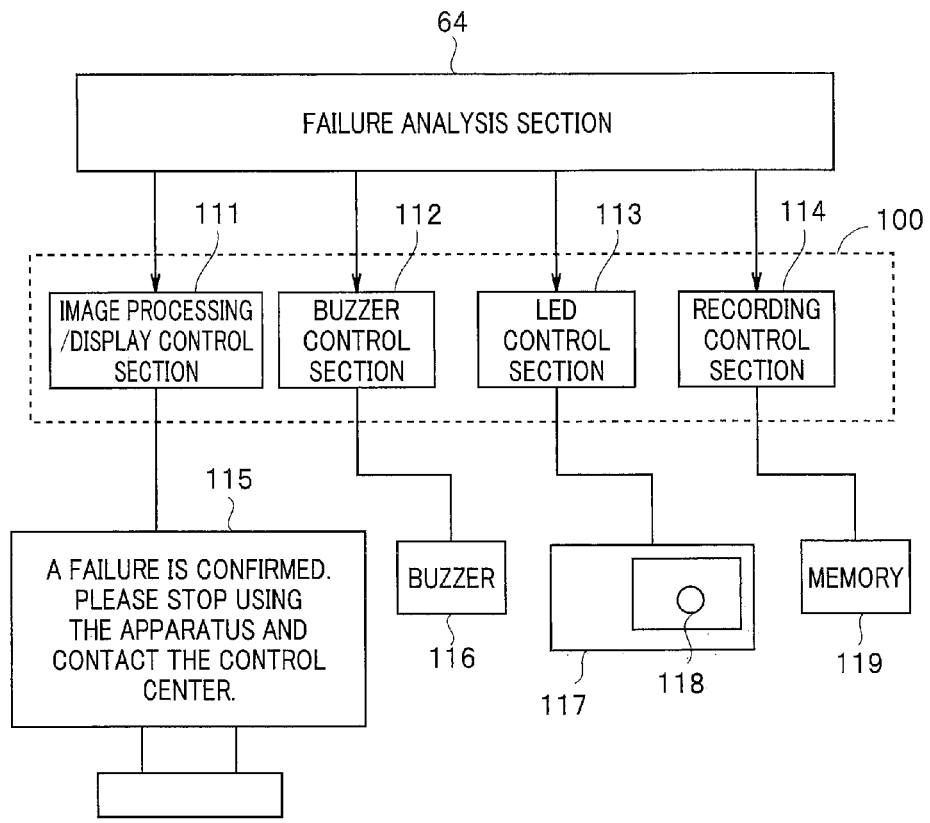
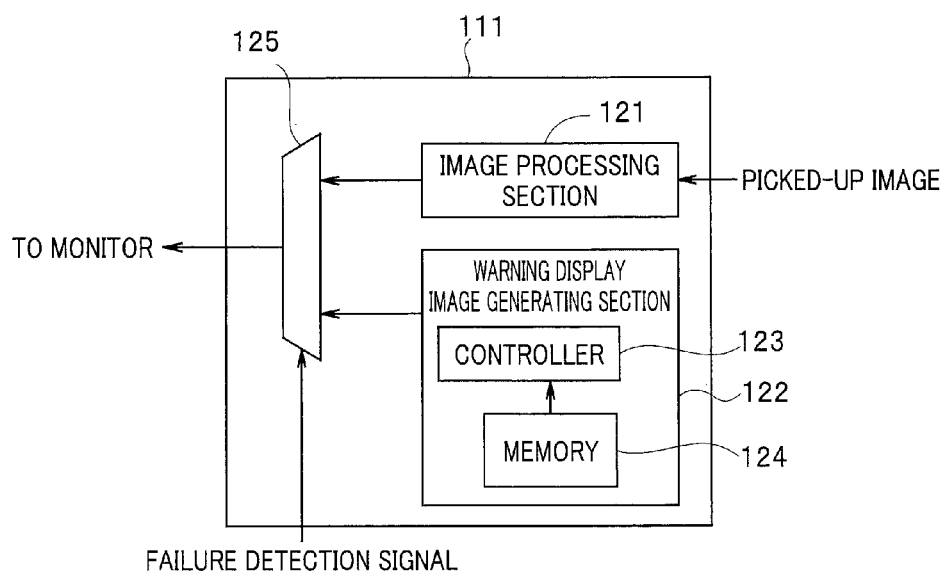

| PWM PULSES FROM CONTROL SECTION | FIXED PWM PULSES | COMPARATOR POSITIVE PHASE TERMINAL | COMPARATOR NEGATIVE PHASE TERMINAL | COMPARATOR OUTPUT |
|---|---|---|---|---|
| OFF(0V) | OFF(0V) | 0V | 1V | 0V |
| OFF(0V) | ON(1V) | 0V | 2V | 0V |
| ON(3.3V) | OFF(0V) | NONOCCURRENCE | | |
| ON(3.3V) | ON(1V) | 3.3V | 2V | POWER SUPPLY VOLTAGE |

LIGHT SOURCE SYSTEM

CROSS REFERENCE TO RELATED APPLICATION

This application is a continuation application of PCT/JP2013/064049 filed on May 21, 2013 and claims benefit of Japanese Application No. 2012-194428 filed in Japan on Sep. 4, 2012, the entire contents of which are incorporated herein by this reference.

BACKGROUND OF INVENTION

1. Field of the Invention

The present invention relates to a light source system suitable for an endoscope.

2. Description of the Related Art

There has been widely used an endoscope which is configured such that the endoscope having an elongated shape is inserted into a body cavity or the like and observation of a region to be examined and various treatments thereof are performed. In such an endoscope, a light source system is adopted for picking up an image inside the cavity. As the light source system, a light emitting portion such as an LED may be provided at a distal end portion of an insertion portion of the endoscope. Such an LED emits light by drive pulses from a video processor for driving the endoscope.

The video processor is configured to control light emission of the LED by a PWM drive in which a duty ratio of the drive pulses is varied. Since the LED has a characteristic of causing temperature rise with the light emission, measures for heat dissipation are taken in the endoscope such as adopting a ceramic substrate having high heat conductivity, for example, in order to prevent the temperature rise of the LED. Further, in Japanese Patent Laid-Open Publication No. 2007-252516, a technique of controlling a light amount of the LED in accordance with a detection result of a temperature sensor is adopted for heat generation control of the endoscope.

Incidentally, heat dissipation characteristics of the endoscopes are different for each endoscope. Therefore, the video processor is conventionally configured such that the temperature rise of the LED is not greater than a temperature defined for each endoscope by controlling a duty ratio of the drive pulses of the LED in accordance with the heat dissipation characteristic of each endoscope.

As mentioned, the heat dissipation characteristics change in accordance with types of the endoscopes. Therefore, the video processor detects a type of a connected endoscope and determines the duty ratio of the drive pulses based on a detection result.

SUMMARY OF THE INVENTION

A light source system according to an aspect of the present invention includes an endoscope having an illumination section in which a pulse-driven light source is configured, and an illumination control section detachably connected to the endoscope and provided with a drive circuit that generates drive pulses for pulse-driving the light source, the light source system comprising: a connection section that detachably connects the endoscope and the illumination control section; a type information generating section that is provided at the endoscope and generates type information regarding the endoscope; a signal generating section that is provided at the endoscope and generates a signal indicative of a duty ratio of the drive pulses which is permitted to the illumination section, the duty ratio being defined in accordance with a type of the endoscope and corresponding to the type information; an endoscope type discriminating section that is provided at the illumination control section, receives the type information from the type information generating section through the connection section and discriminates the type of the endoscope based on the received type information; a light adjusting section that is provided at the illumination control section and outputs light-adjusted drive pulses having a duty ratio not greater than a permissible duty ratio permitted to the illumination section in accordance with information based on a discrimination result from the endoscope type discriminating section; and a limiting section that is provided at the illumination control section, and to which the light-adjusted drive pulses from the light adjusting section and the signal indicative of the duty ratio of the drive pulses which is permitted to the illumination section are inputted, the limiting section limiting the light-adjusted drive pulses inputted from the light adjusting section to have a duty ratio not greater than a duty ratio based on the signal from the signal generating section, and providing limited pulses to the drive circuit to output the drive pluses.

BRIEF DESCRIPTION OF THE DRAWINGS

FIG. 6 is a block diagram showing a specific example of a warning control section 100;

FIG. 7 is a block diagram of an example of a specific configuration of an image processing/display control section 111;

DETAILED DESCRIPTION OF THE PREFERRED EMBODIMENT(S)

Figure 1:
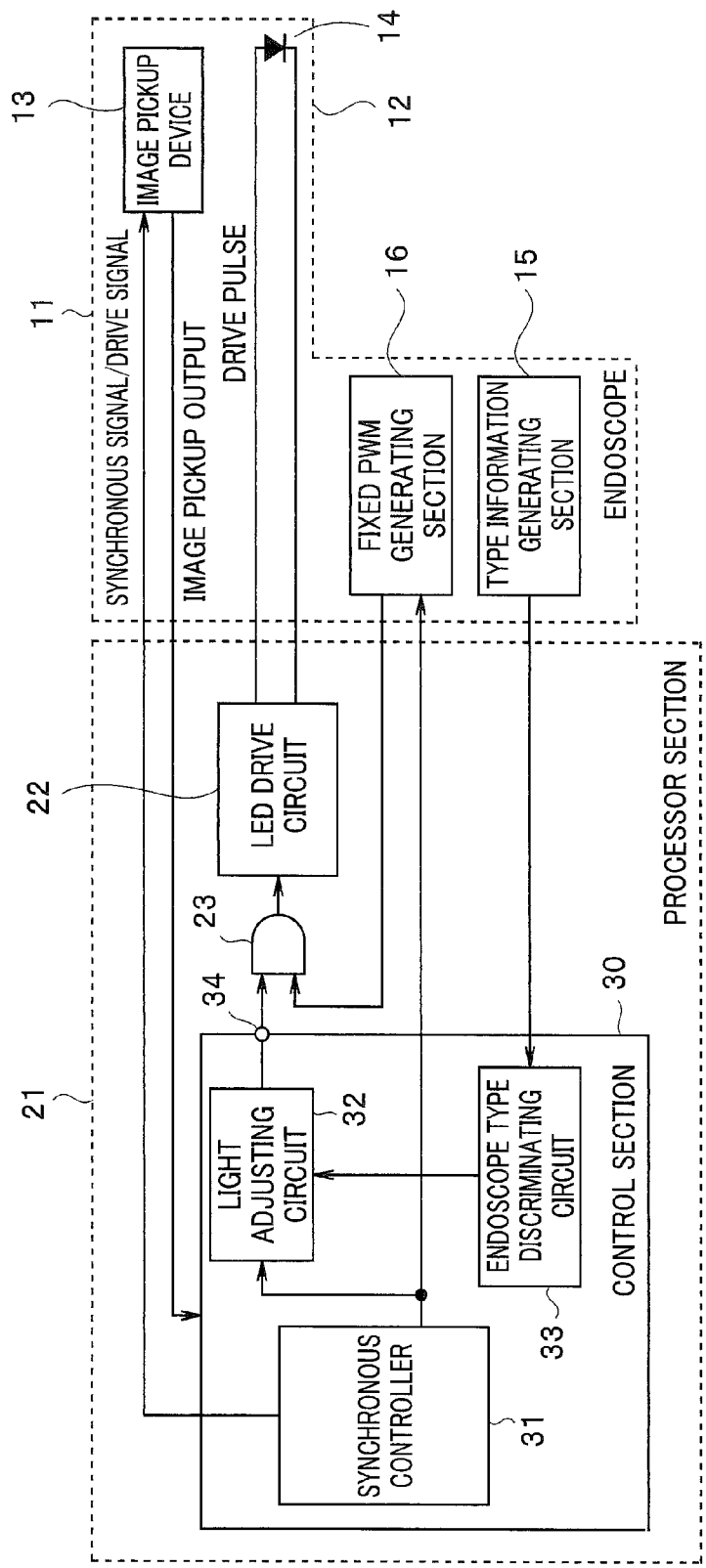
FIG. 1 is a block diagram showing a light source system according to a first embodiment of the present invention.

Hereinafter, embodiments of the present invention will be described referring to the drawings.

First Embodiment

FIG. 1 is a block diagram showing a light source system according to a first embodiment of the present invention. The present embodiment is directed to a configuration in which a light source system is applied to an endoscope apparatus constituted by an endoscope and a processor section. It is noted that the light source system in the present embodiment is applicable to all systems in which an illumination section having a pulse-driven light source and an illumination control section that controls the illumination section are configured to be detachable from each other.

The endoscope apparatus is configured by an endoscope 11 which constitutes an illumination section and a processor section 21 which constitutes an illumination control section. The endoscope 11 has an insertion portion 12 which is elongated and insertable into a lumen or the like, and a proximal end side of the insertion portion 12 is configured to be detachably connected to the processor section 21 by a connector which is not shown. Thus, it is configured such that the processor section 21 can be connected to endoscopes of different types.

An image pickup device 13 for picking up a video image of an object such as an interior of a lumen, and an LED 14 which constitutes a light source are disposed at a distal end of the insertion portion 12. The LED 14 is configured to be driven by an LED drive circuit 22 and capable of irradiating the object with illumination light. The image pickup device 13 is configured by a CCD, a CMOS sensor or the like, has an image pickup surface on which return light from the object is incident, performs photoelectric conversion of an entered optical image of the object, and sequentially outputs image pickup outputs based on accumulated electric charge.

The image pickup device 13 operates by being supplied with a drive signal including a synchronous signal by a synchronous controller 31 disposed in a control section 30, and supplies the image pickup outputs to the processor section 21. Besides, it is configured that the image pickup outputs are processed in the processor section 21 and an endoscopic image can be displayed based on the image pickup outputs on a display section which is not shown, but a processing circuit which processes the image pickup outputs and the display section are omitted in FIG. 1.

In the control section 30, the synchronous controller 31, a light adjusting circuit 32 and an endoscope type discriminating circuit 33 are configured. The control section 30 can be configured for example by a DSP (Digital Signal Processing), an FPGA (Field Programmable Gate Array) or the like. The synchronous controller 31 generates the synchronous signal for controlling respective portions. To the light adjusting circuit 32, the synchronous signal is supplied from the synchronous controller 31 and the light adjusting circuit 32 generates PWM pulses for pulse-driving the LED 14 to be synchronized with the synchronous signal. The light adjusting circuit 32 may be configured to generate the PWM pulses in synchronism with scanning of the image pickup device 13. The PWM pulses from the light adjusting circuit 32 are outputted through an output terminal 34 of the control section 30.

In the present embodiment, the PWM pulses from the control section 30 are supplied to the LED drive circuit 22 through an AND circuit 23. The LED drive circuit 22 generates drive pulses based on the inputted PWM pulses and supplies the generated drive pulses to the LED 14. The LED 14 emits light by being driven by the drive pulses. The LED 14 emits light by a light emission amount in accordance with a duty ratio of the drive pulses, i.e. a duty ratio of the PWM pulses. Therefore, light adjusting control of the LED 14 can be performed by controlling the duty ratio of the PWM pulses outputted from the light adjusting circuit 32.

The LED 14 generates heat of a calorific value in accordance with the light emission amount. In order to manage the calorific value of the LED 14 for each endoscope, the endoscope type discriminating circuit 33 provided in the control section 30 of the processor section 21 discriminates a type of the endoscope being connected. For this discrimination, the endoscope type discriminating circuit 33 obtains type information from the endoscope 11. A type information generating section 15 is provided in the endoscope 11. The type information generating section 15 can be configured by a memory, a mechanical jumper switch or the like, and is configured to be capable of generating the type information regarding the type of the endoscope and supplying the information to the processor section 21 being connected.

The endoscope type discriminating circuit 33 discriminates the type of the endoscope presently connected based on inputted type information, and outputs information on the basis of a discrimination result to the light adjusting circuit 32. As described, an endoscope has a heat dissipation characteristic different for each type of the endoscope, and a calorific value permitted as a calorific value of the LED 14 is defined in accordance with the heat dissipation characteristic, and an upper limit of the duty ratio (hereinafter referred to as "permissible duty ratio") of the drive pulses of the LED 14 is defined for each type of the endoscope in accordance with the calorific value.

The light adjusting circuit 32 determines the upper limit of the duty ratio of the PWM pulses to be generated, in accordance with the information on the basis of the discrimination result from the endoscope type discriminating circuit 33. Thereby, the light adjusting circuit 32 can output the PWM pulses having the duty ratio not greater than the permissible duty ratio in accordance with the type of the endoscope 11 being connected. In this manner, the light adjusting circuit 32 is capable of controlling the light emission amount and the calorific value of the LED 14 for each type of the endoscope.

Incidentally, it can be conceived that the type of the endoscope being connected is mistaken in the endoscope type discriminating circuit 33 as in a case of failing in receiving the type information, or the like. In this case, there is a possibility that the light adjusting circuit 32 generates PWM pulses having a duty ratio greater than the permissible duty ratio which is permitted for each type of the endoscope 11 being connected. Further, the output terminal 34 of the control section 30 is fixed to be in H level by a failure of the output terminal 34. In this case also, it can be conceived that the PWM pulses having the duty ratio greater than the permissible duty ratio of the endoscope 11 are outputted from the control section 30.

Therefore, in the present embodiment, it is configured such that the duty ratio of the PWM pulses to be supplied to the LED drive circuit 22 is limited to be not greater than the permissible duty ratio which is permitted to the endoscope connected to the processor section 21 so that the light emission amount and the calorific value of the LED 14 are within ranges of values permitted to the endoscope, irrespective of a failure or an erroneous detection. For such control of the duty ratio, the AND circuit 23 as a control section and a fixed PWM generating section 16 as a signal generating section are provided.

To the fixed PWM generating section 16, the synchronous signal from the synchronous controller 31 is given and the fixed PWM generating section 16 is configured to generate fixed PWM pulses having a duty ratio equal to the permissible duty ratio which is permitted to the endoscope 11 to be synchronized with the synchronous signal and to output the generated pulses to the AND circuit 23. That is, the fixed PWM generating section 16 generates the fixed PWM pulses having the permissible duty ratio which is defined in accordance with the type of the endoscope for each of the endoscopes. It is noted that the fixed PWM generating section 16 may be configured to generate the PWM pulses in synchronism with the scanning of the image pickup device 13. In the present embodiment, it is merely needed that the fixed PWM pulses from the fixed PWM generating section 16 and the PWM pulses from the light adjusting circuit 32 are synchronized with each other.

The AND circuit 23 is configured to obtain an AND operation result of the PWM pulses from the control section 30 and the fixed PWM pulses from the fixed PWM generating section 16 provided in the endoscope 11, and supply the AND operation result to the LED drive circuit 22. The duty ratio of the pulses supplied to the LED drive circuit 22 is limited to be not greater than the duty ratio of the fixed PWM pulses of the fixed PWM generating section 16.

Figure 2:
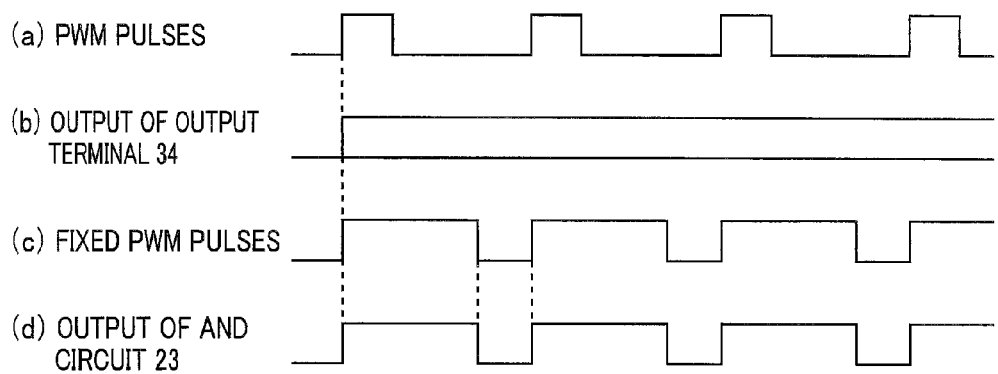
FIG. 2 is a timing chart for explaining an operation of the first embodiment.

Next, an operation of the embodiment as configured above will be described referring to the time chart of FIG. 2. FIG. 2(*a*) shows PWM pulses generated by the light adjusting circuit 32, FIG. 2(*b*) shows an output of the output terminal 34, FIG. 2(*c*) shows an output of the fixed PWM generating section 16, and FIG. 2(*d*) shows an output of the AND circuit 23.

Now, it is assumed that the PWM pulses shown in FIG. 2(*a*) are generated by the light adjusting circuit 32. FIG. 2(*c*) shows the fixed PWM pulses, the duty ratio of the PWM pulses shown in FIG. 2(*a*) is smaller than the permissible duty ratio and the output of the light adjusting circuit 32 is normal. The PWM pulses of the light adjusting circuit 32 are supplied from the output terminal 34 to the LED drive circuit 22 through the AND circuit 23. The LED drive circuit 22 generates the drive pulses having the same frequency and the same duty ratio as the inputted PWM pulses and supplies the generated drive pulses to the LED 14. Thus, the LED 14 is pulse driven and emits light by the light emission amount in accordance with the duty ratio of the PWM pulses.

Here, it is assumed that the output of the output terminal 34 is fixed to be in H level by a failure of the output terminal 34, for example, as shown in FIG. 2(*b*). If the output of the output terminal 34 is supplied to the LED drive circuit 22 as it is, the duty ratio of the output of the LED drive circuit 22 becomes 100% and the calorific value of the LED 14 exceeds the calorific value permitted to the endoscope 11.

In the present embodiment, the output of the output terminal 34 is supplied to the AND circuit 23, and the AND circuit 23 supplies an AND operation result of the output from the output terminal 34 and the fixed PWM pulses from the fixed PWM generating section 16 to the LED drive circuit 22. Since the fixed PWM pulses from the fixed PWM generating section 16 are pulses having the permissible duty ratio, the output of the AND circuit 23 becomes an output having a duty ratio not greater than the permissible duty ratio. As shown in FIG. 2(*d*), in the case where the output of the output terminal 34 is fixed to be in H level, the output of the AND circuit 23 becomes pulses having a duty ratio which coincides with the permissible duty ratio.

In this manner, the pulses having the duty ratio not greater than the permissible duty ratio are inputted to the LED drive circuit 22, irrespective of presence or absence of a failure, and the calorific value of the LED 14 is limited to be not greater than the calorific value permitted to the endoscope 11.

Besides, the PWM pulses from the light adjusting circuit 32 and the fixed PWM pulses from the fixed PWM generating section 16 are generated in synchronism with the synchronous signal from the synchronous circuit 31 and, when there occurs no failure in the output terminal 34, the PWM pulses from the light adjusting circuit 32 are given to the LED drive circuit 22 as they are. Further, when an error occurs in discrimination of the endoscope type, or PWM pulses having a duty ratio greater than the permissible duty ratio are outputted from the light adjusting circuit 32, the pulses having the permissible duty ratio of the fixed PWM pulses are supplied to the LED drive circuit 22 by the AND circuit 23.

As described, in the present embodiment, it is configured that the fixed PWM generating section that generates the fixed PWM pulses having the permissible duty ratio which corresponds to the calorific value defined for the type of each endoscope is provided in each endoscope, and the pulses of the AND operation result of the PWM pulses from the light adjusting circuit and the fixed PWM pulses are supplied to the LED drive circuit, it is possible to drive the LED with the duty ratio not greater than the duty ratio which corresponds to the calorific value permitted to each endoscope, irrespective of erroneous discrimination of the endoscope type and failures in respective components, and it is possible to prevent the LED from generating heat to exceed the calorific value permitted to each endoscope.

Second Embodiment

Figure 3:
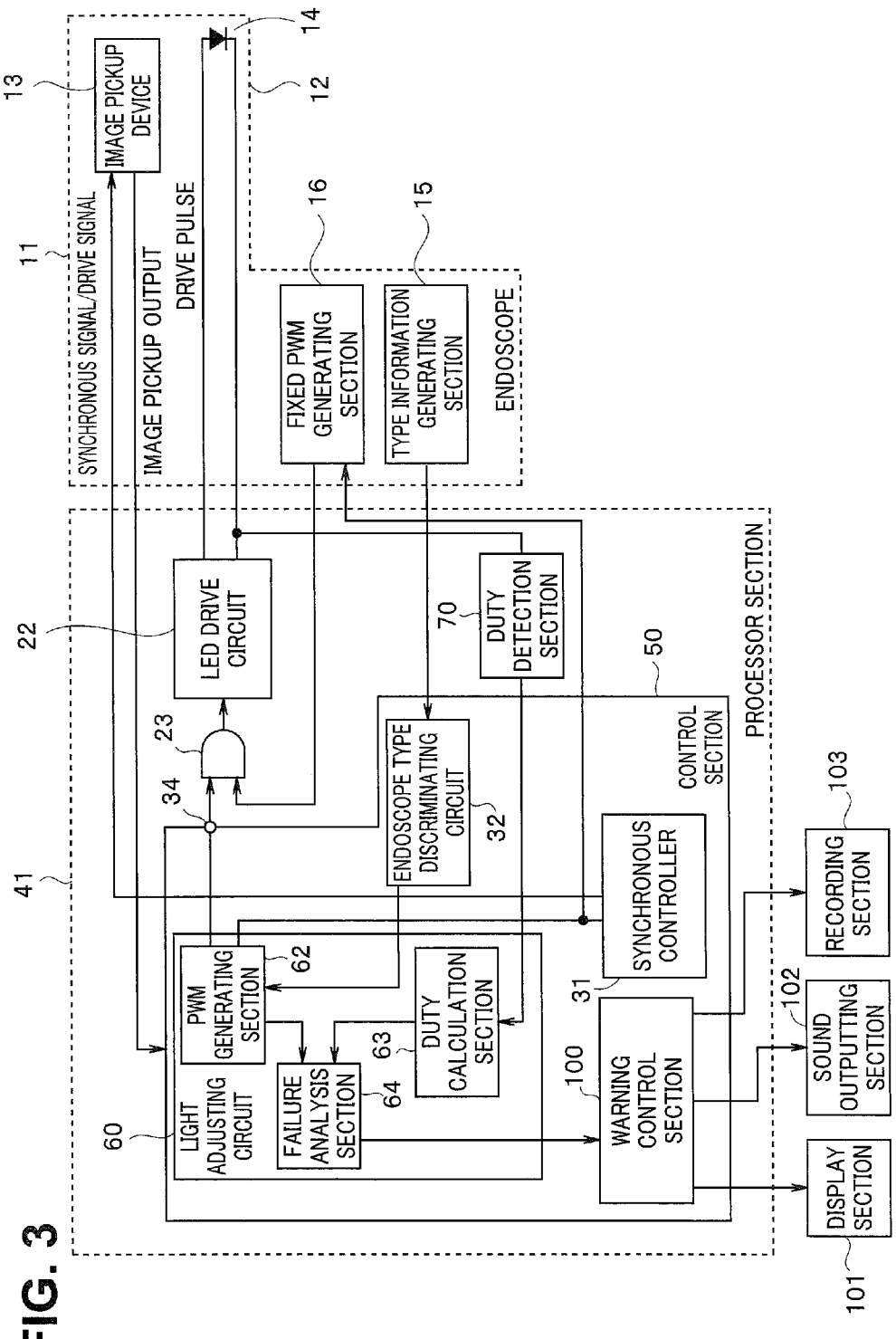
FIG. 3 is a block diagram showing a second embodiment of the present invention.

FIG. 3 is a block diagram showing a second embodiment of the present invention. In FIG. 3, the same reference signs are assigned to the same elements in FIG. 1 and the description thereof is omitted.

The present embodiment enables detection of failures of signal cables and circuits for driving the LED 14. In the present embodiment, a control section 50 is provided in a processor section 41 in place of the control section 30 in FIG. 1, and a duty detection section 70 is added to the processor section 41. In the control section 50, a light adjusting circuit 60 is adopted in place of the light adjusting circuit 32 in FIG. 1 and a warning control section 100 is added.

In the present embodiment also, the light adjusting circuit 60 can be configured by the DSP, the FPGA or the like. In the light adjusting circuit 60, a PWM generating section 62, a duty calculation section 63 and a failure analysis section 64 are configured. To the PWM generating section 62, the synchronous signal is supplied from the synchronous controller 31 and the PWM generating section. 62 generates the PWM pulses for pulse-driving the LED 14 to be synchronized with the synchronous signal. The PWM pulses from the PWM generating section 62 are outputted through the output terminal 34. Further, the PWM generating section 62 determines the upper limit of the duty ratio of the PWM pulses to be generated, in accordance with the information on the basis of the discrimination result from the endoscope type discriminating circuit 33. Thereby, the PWM generating section 62 can output the PWM pulses having the duty ratio not greater than the permissible duty ratio in accordance with the type of the endoscope 11 being connected. In this manner, the PWM generating section 62 is capable of controlling the light emission amount and the calorific value of the LED 14 for each type of the endoscope.

However, it can be conceived that there arises a situation in which the LED 14 is not driven by normal PWM pulses for various reasons such as a short circuit or an open of a signal cable which transmits the drive pulses from the LED drive circuit 22, an erroneous discrimination of the type of the endoscope, a failure of the output terminal 34, a failure of the PWM generating section 62. Therefore, in the present embodiment, it is configured such that a duty ratio of an LED voltage generated in the LED 14 is detected and compared with the PWM pulses, to thereby make it possible to perform analysis of these failures, presentation of an analysis result to an operator and recording of the analysis result.

The duty calculation section 63 in the light adjusting circuit 60 calculates the duty ratio of the LED voltage by digital processing. The duty detection section 70 performs processing of converting the LED voltage into a digital value which can be subjected to the digital processing. That is, the duty detection section 70 is connected to one of a pair of signal lines for supplying the drive pulses from the LED drive circuit 22 to the LED 14 and detects pulses which correspond to the LED voltage.

Figure 4:
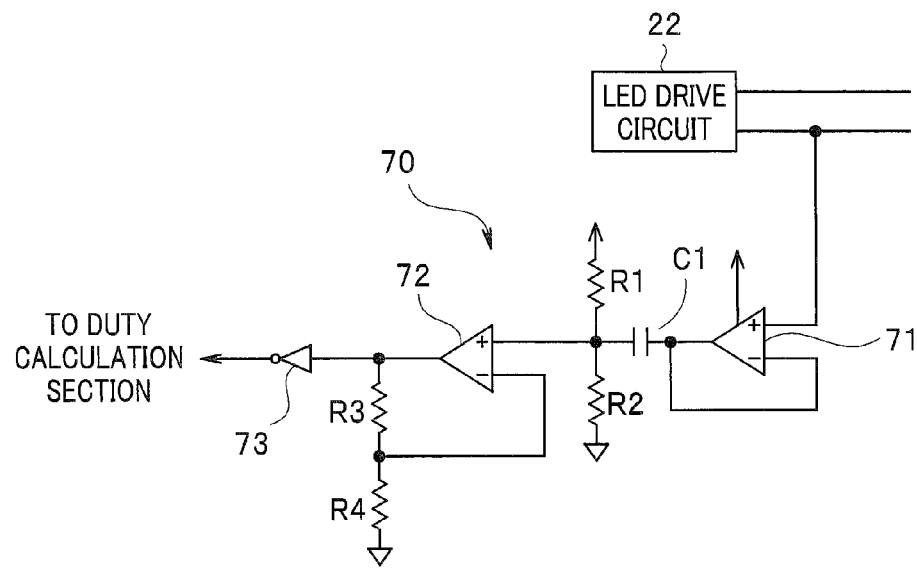
FIG. 4 is a circuit diagram showing an example of a specific circuit configuration of a duty detection section 70 in FIG. 3.
Figure 5:
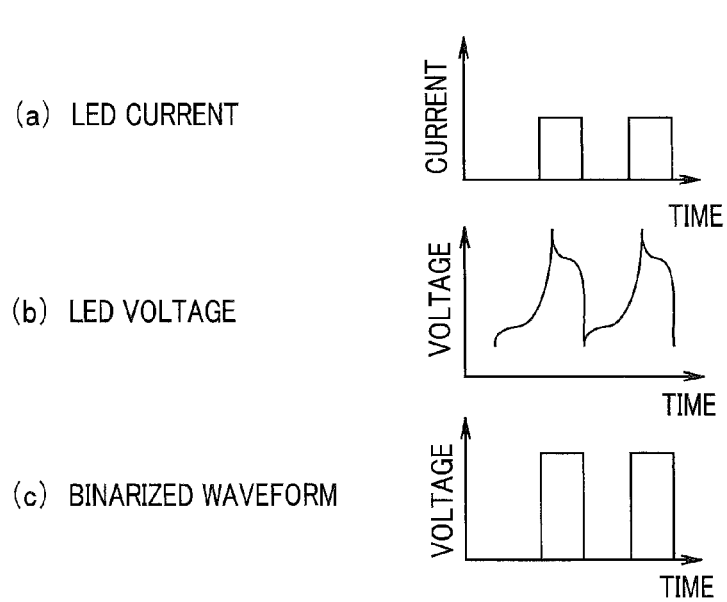
FIG. 5 is a waveform diagram showing signal waveforms of respective portions in FIG. 4.

FIG. 4 is a circuit diagram showing an example of a specific circuit configuration of the duty detection section 70 in FIG. 3. FIG. 5 is a waveform diagram showing signal waveforms of respective portions in FIG. 4.

One of a pair of signal cables for supplying the drive pulses from the LED drive circuit 22 to the LED 14 (a cathode cable of the LED 14 in FIG. 4) is connected to a positive phase input terminal of an operational amplifier 71. FIG. 5(a) shows a waveform of an LED current flowing in the LED 14, and FIG. 5(b) shows a waveform of the LED voltage.

An output terminal of the operational amplifier 71 is connected to a negative phase input terminal and the operational amplifier 71 operates as an impedance converter. The operational amplifier 71 has the input terminals of high impedance and takes out the LED voltage shown in FIG. 5(b) from the signal cable. The output terminal of the operational amplifier 71 is connected to a positive phase input terminal of an operational amplifier 72 through a condenser C1. As shown in FIG. 5(b), a bias is added to the LED voltage and a bias component thereof is removed by an AC coupling by the condenser C1.

The positive phase input terminal of the operational amplifier 72 is connected to a connection point of resistors R1 and R2. The resistors R1 and R2 are connected to respective power supply terminals and the connection point of the resistors R1 and R2 is biased to have a predetermined voltage. An output terminal of the operational amplifier 72 is connected to a power supply terminal through resistors R3 and R4 and a connection point of the resistors R3 and R4 is connected to a negative phase input terminal of the operational amplifier 72. An amplifier is configured by the operational amplifier 72 and the resistors R3 and R4, and by this amplifier, the condenser C1 and the resistors R1 and R2, an output of the operational amplifier 71 is biased and amplified to be converted into a signal waveform in which amplitude thereof varies within a predetermined level range.

The output terminal of the operational amplifier 72 is supplied to an inverter 73. The output terminal of the operational amplifier 72 is binarized to be an H level or an L level as shown in FIG. 5(c) by the inverter 73, and then supplied to the duty calculation section 63. Besides, a buffer may be adopted in place of the inverter 73. In this manner, the duty ratio of the drive pulses from the LED drive circuit 22 is made possible to be detected.

The duty calculation section 63 calculates the duty ratio by counting an H level period and an L level period of an output of the duty detection section 70. A calculation result of the duty calculation section 63 is supplied to the failure analysis section 64. To the failure analysis section 64, information of the duty ratio of the PWM pulses generated by the PWM generating section 62 is also given.

The failure analysis section 64 compares the duty ratio obtained by the duty calculation section 63 and the duty ratio of the PWM pulses generated by the PWM generating section 62. Thereby, analysis of the failure is performed. The failure analysis section 64 determines that there is no failure if the duty ratio obtained by the duty calculation section 63 coincides with the duty ratio of the PWM pulses generated by the PWM generating section 62. The failure analysis section 64 determines that there is a failure if these duty ratios do not coincide with each other.

For example, the failure analysis section 64 can detect that the output of the duty detection section 70 does not have a toggle waveform in which the H level and the L level are repeated, from the output of the duty ratio calculation section 63. That is, when the output of the duty detection section 70 is fixed to be in H level or in L level, the failure analysis section 64 determines a short circuit failure of the signal cables for supplying the drive pulses to the LED 14. It is noted that the failure analysis section 64 determines different failure modes in dependence on whether the output of the duty detection section 70 is fixed to be in H level or in L level.

Further, the failure analysis section 64, if the duty ratio obtained by the duty calculation section 63 does not coincide with the duty ratio of the PWM pulses generated by the PWM generating section 62, determines a failure mode which is different from the case where the output of the duty detection section 70 does not have the toggle waveform.

An analysis result of the failure analysis section 64 is supplied to the warning control section 100. The warning control section 100 presents an inputted analysis result of the failure to a user. For example, the warning control section 100 converts the analysis result into a form capable of image display, a form capable of sound output or a form capable of recording, and outputs the form to a display section 100, a sound outputting section 102, a recording section 103, or the like.

FIG. 6 is a block diagram showing a specific example of the warning control section 100. FIG. 7 is a block diagram of an example of a specific configuration of an image processing/display control section 111. The warning control section 100 is configured by the image processing/display control section 111, a buzzer control section 112, an LED control section 113 and a recording control section 114, etc. It is noted that a monitor 115 and an LED 118 in FIG. 6 correspond to the display section 101 in FIG. 3 and a buzzer 116 corresponds to the sound output section 102 and a memory 119 corresponds to the recording section 103.

The image processing/display control section 111 is constituted by an image processing section 121 and a warning display image generating section 122. To the image processing section 121, a picked-up image (not shown) is supplied from the image pickup device 13. The image processing section 121 outputs an inputted picked-up image to a selector 125 after performing predetermined video signal processing with respect to the inputted picked-up image.

The warning display image generating section 122 is constituted by a controller 123 and a memory 124. In the memory 124, image information for performing a warning display is stored. The controller 123 generates a display image for performing an image display of the information read from the memory 124 and outputs the display image to the selector 125.

To the selector 125, a failure detection signal indicative of presence or absence of the failure is inputted from the failure analysis section 64. The selector 125 selects and outputs the display image from the warning display image generating section 122 by the failure detection signal indicative of presence of the failure, and selects and outputs the picked-up image from the image processing section 121 by the failure detection signal indicative of absence of the failure. An output of the selector 125 is supplied to the monitor 115.

Thereby, a warning message such as "A failure is confirmed. Please stop using the apparatus and contact the control center." can be displayed on a display screen of the monitor 125.

The buzzer control section 112 causes the buzzer 116 to perform a sound output of a buzzer when the failure detection signal indicative of presence of the failure is inputted. The LED control section 113 causes the LED 118 on a front panel 117 to perform a blinking display. Further, the recording control section 114 converts the inputted analysis result into recording data to be recorded and gives the converted data to the memory 119. Thereby, the analysis result of the failure is recorded in the memory 119. It is noted that a nonvolatile memory can be adopted as the memory 103.

Besides, it may be configured that the control section 50 automatically performs one or more measures of stopping of the LED drive circuit, stopping of power supply to the endoscope, a failure notice to the user, etc. in accordance with the failure mode shown by the analysis result of the failure analysis section 64.

As described, in the present embodiment, the same effects as those of the first embodiment can be obtained, and also it is possible to detect a failure in the signal cables or the circuits for driving the LED, to analyze a type of the failure and to present an analysis result thereof to the user.

Incidentally, in the above embodiments, the PWM pulses from the control section 30 or 50 and the fixed PWM pulses are given to the AND circuit, and thereby it is controlled such that the duty ratio of the drive pulses is not greater than the duty ratio of the fixed PWM pulses. The AND circuit 23 is used for limiting the duty ratio, but it is possible to use other devices. For example, a bus switch for switching a bus line at high speed may be used in place of the AND circuit 23.

Figure 8:
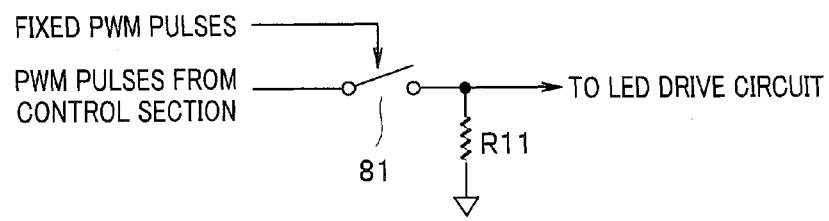
FIG. 8 is a circuit diagram showing a configuration in which a bus switch is used.

FIG. 8 is a circuit diagram showing a configuration in a case of using the bus switch. The PWM pulses from the control section 30 or 50 are supplied to the LED drive circuit 22 through a bus switch 81. The bus switch 81 is subjected to on/off control by the fixed PWM pulses, and turns on when the fixed PWM pulse is in H level and turns off when the fixed PWM pulse is in L level. In a period when the fixed. PWM pulse is in L level, an output of the bus switch 81 is in L level. That is, only in a period when the fixed PWM pulse is in H level, the H level is transmitted and the duty ratio of the pulses supplied to the LED drive circuit 22 is limited to be not greater than the duty ratio of the fixed PWM pulses.

Figure 9:
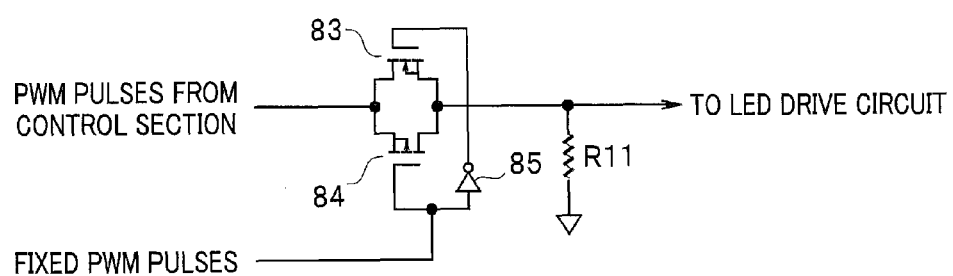
FIG. 9 is a circuit diagram showing a configuration in which transistors 83, 84 and an inverter 85 are adopted in place of a bus switch 81 in FIG. 8.

FIG. 9 is a circuit diagram showing a configuration in which transistors 83, 84 and an inverter 85 are adopted in place of the bus switch 81. To a gate of a P-type transistor 84, the fixed PWM pulses are supplied as they are, and to a gate of an N-type transistor 83, inverted pulses of the fixed PWM pulses by the invertor 85 are supplied. The transistors 83 and 34 turn on when the fixed PWM pulse is in H level to transmit the PWM pulse from the control section 30 or 50 to the LED drive circuit 22, and turn off when the fixed PWM pulse is in L level to block the transmission of the PWM pulse. Thereby, the duty ratio of the pulses supplied to the LED drive circuit 22 is limited to be not greater than the duty ratio of the fixed PWM pulses.

Figures 10, 11:
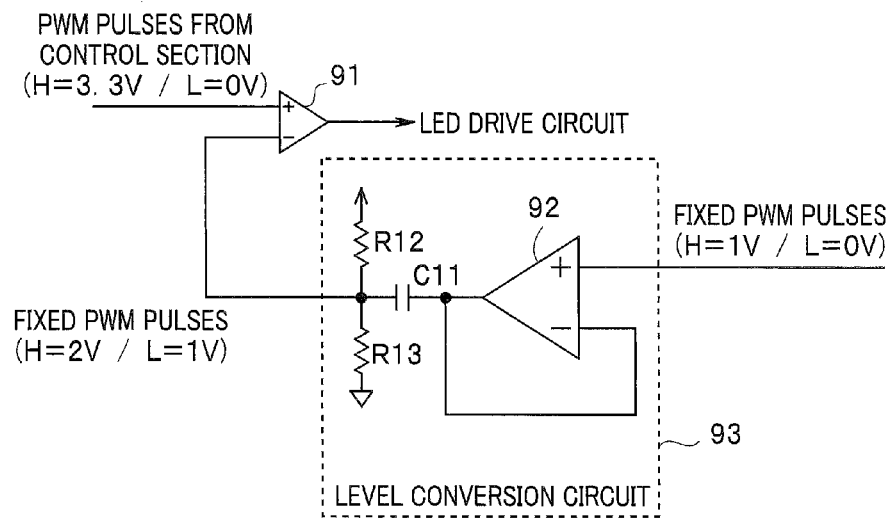
FIG. 10 is a circuit diagram showing an example in which a circuit by a comparator 91 and an amplifier 92 is adopted in place of an AND circuit 23.
FIG. 11 is a diagram for explaining an operation in the example of FIG. 10.

FIG. 10 is a circuit diagram showing an example in which a circuit by a comparator 91 and an amplifier 92 is adopted in place of the AND circuit 23. In the example of FIG. 10, the description will be given assuming that the H level and the L level of the PWM pulses from the control section 30 or 50 are 3.3V and 0V, respectively, and the H level and the L level of the fixed PWM pulses from the type information generating section 15 are 1V and 0V, respectively. FIG. 11 is a diagram for explaining an operation in the example of FIG. 10. It is noted that "ON" indicates the H level and "OFF" indicates the L level in FIG. 11.

Since the duty ratio of the fixed PWM pulses is the permissible duty ratio, the fixed PWM pulse does not become L level in a period when the PWM pulse from the control section 30 or 50 is in H level. The fixed PWM pulse of 0V is converted into a pulse of 1V by a level conversion circuit 93 constituted by the amplifier 92, a condenser C11 and resistors R12, R13. Further, the fixed PWM pulse of 1V is converted into a pulse of 2V by the level conversion circuit 93.

In a period when the PWM pulse of 0V (L level) is supplied to a positive phase input terminal of the comparator 91, the fixed PWM pulse of 1V (L level) or 2V (H level) is inputted to an inverse phase input terminal of the comparator. In this case, an output of the comparator 91 is at 0V.

In a period when the PWM pulse of 3.3V (H level) is supplied to the positive phase input terminal of the comparator 91, the fixed PWM pulse of 2V (H level) is surely inputted to the inverse phase input terminal of the comparator. In this case, the output of the comparator 91 is at a power supply voltage (H level).

In this manner, the duty ratio of the pulses supplied to the LED drive circuit 22 is limited to be not greater than the duty ratio of the fixed PWM pulses.

Figure 12:
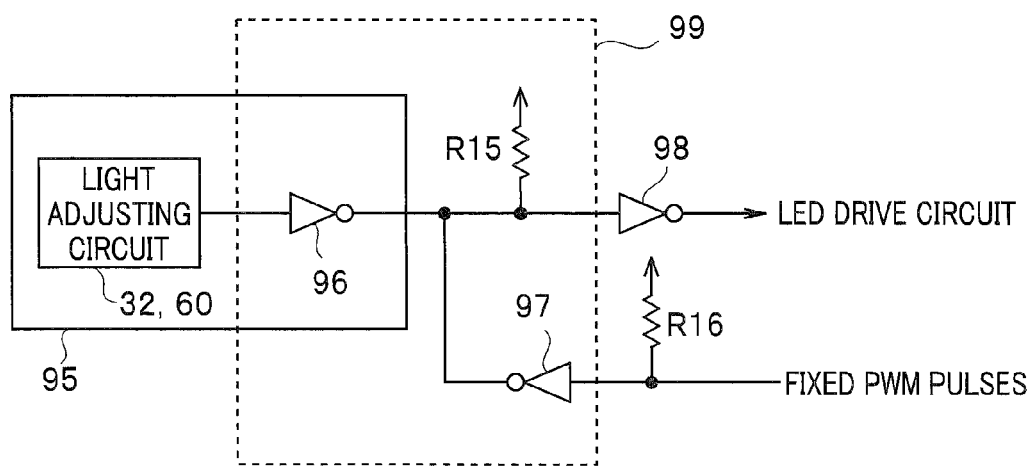
FIG. 12 is a circuit diagram showing an example in which a wired OR circuit 99 is adopted in place of the AND circuit 23.

FIG. 12 is a circuit diagram showing an example in which a wired OR circuit 99 is adopted in place of the AND circuit 23. In the case of the example of FIG. 12, it is assumed that the light adjusting circuit 32 or 60 generates the PWM pulse in L level in a period when power is supplied to the LED 14 (hereinafter referred to as "ON period"), and generate the PWM pulse in H level in a period when power is not supplied to the LED (hereinafter referred to as "OFF period"). Likewise, it is assumed that the fixed PWM pulse is in L level in the ON period and in H level in the OFF period.

The PWM pulses from the light adjusting circuit 32 or 60 are outputted to an inverter 98 through an open-drain output transistor 96. Further, the fixed PWM pulses are supplied to the inverter 98 through an open-drain output transistor 97. It is noted that the light adjusting circuit 32 or 60 and the transistor 96 are configured in a DSP 95.

Output terminals of the open-drain output transistors 96 and 97 are connected to a power supply terminal through a pull-up resistor R15 and the wired OR circuit 99 is configured by the transistors 96 and 97 and the pull-up resistor R15. An output of the wired OR circuit 99 is inverted by the inverter 98 and then supplied to the LED drive circuit 22. It is noted that an input terminal of the transistor 97 is connected to the power supply terminal through a pull-up resistor R16 so as to maintain an input of the LED drive circuit 22 to be in L level when the endoscope is not connected.

The output of the wired OR circuit 99 is in L level in a L level period of the PWM pulse from the light adjusting circuit 32 or 60 and in a L level period of the fixed PWM pulses. The pulse in L level is inverted by the inverter 98 and supplied to the LED drive circuit 22 so that the power is supplied to the LED 14.

Further, the output of the wired OR circuit 99 is in H level in an H level period of the fixed PWM pulse, irrespective of logic values of the PWM pulses from the light adjusting circuit 32 or 60. Therefore, in the H level period of the fixed PWM pulse, the L level is supplied to the LED drive circuit 22 and the duty ratio of the drive pulses is limited by the H level period of the fixed PWM pulse. In this manner, the duty ratio of the pulses supplied to the LED drive circuit 22 is limited to be not greater than the duty ratio of the fixed PWM pulses.

What is claimed is:

1. A light source system including an endoscope having an illumination section in which a pulse-driven light source is configured, and an illumination control section detachably connected to the endoscope and provided with a drive circuit that generates drive pulses for pulse-driving the light source, the light source system comprising:

a connection section that detachably connects the endoscope and the illumination control section;

a type information generating section that is provided at the endoscope and generates type information regarding the endoscope;

a signal generating section that is provided at the endoscope and generates a signal indicative of a duty ratio of the drive pulses which is permitted to the illumination section, the duty ratio being defined in accordance with a type of the endoscope and corresponding to the type information;

an endoscope type discriminating section that is provided at the illumination control section, receives the type information from the type information generating section through the connection section and discriminates the type of the endoscope based on the received type information;

a light adjusting section that is provided at the illumination control section and outputs light-adjusted drive pulses having a duty ratio not greater than a permissible duty ratio permitted to the illumination section in accordance with information based on a discrimination result from the endoscope type discriminating section; and a limiting section that is provided at the illumination control section, and to which the light-adjusted drive pulses from the light adjusting section and the signal indicative of the duty ratio of the drive pulses which is permitted to the illumination section are inputted, the limiting section limiting the light-adjusted drive pulses inputted from the light adjusting section to have a duty ratio not greater than a duty ratio based on the signal from the signal generating section, and providing limited pulses to the drive circuit to output the drive pluses.

2. The light source system according to claim 1, wherein the drive circuit generates the drive pulses having a duty ratio which coincides with a duty ratio of the light-adjusted drive pulses, the signal generating section generates pulses having a duty ratio which coincides with the duty ratio of the drive pulses which is permitted to the illumination section, and the limiting section supplies the light-adjusted drive pulses to the drive circuit in periods permitted by the pulses of the signal generating section.

3. The light source system according to claim 2, wherein the limiting section comprises an AND circuit that supplies an AND operation result of the pulses of the signal generating section and the light-adjusted drive pulses to the drive circuit.

4. The light source system according to claim 2, wherein the limiting section comprises a bus switch that supplies the light-adjusted drive pulses to the drive circuit in periods permitted by the pulses of the signal generating section.

5. The light source system according to claim 2, wherein the limiting section supplies the light-adjusted drive pulses to the drive circuit in periods permitted by the pulses of the signal generating section by a switch circuit constituted by a transistor and an inverter.

6. The light source system according to claim 2, wherein the limiting section supplies the light-adjusted drive pulses to the drive circuit in periods permitted by the pulses of the signal generating section by a pulse generating circuit constituted by a comparator and an amplifier.

7. The light source system according to claim 2, wherein the limiting section supplies the light-adjusted drive pulses to the drive circuit in periods permitted by the pulses of the signal generating section by a pulse generating circuit constituted by a wired OR circuit.

8. The light source system according to claim 2, comprising
a waveform conversion section that converts a lamp voltage of the light source into a rectangular wave; and
a failure analysis section that analyzes a failure by comparing a duty ratio of an output of the waveform conversion section and a duty ratio of the drive pulses from the drive circuit.

9. The light source system according to claim 8, comprising a display control section for displaying an analysis result of the failure analysis section.

10. The light source system according to claim 8, comprising a recording control section for recording an analysis result of the failure analysis section.

11. The light source system according to claim 1, comprising:
a waveform conversion section that converts a lamp voltage of the light source into a rectangular wave; and
a failure analysis section that analyzes a failure by comparing a duty ratio of an output of the waveform conversion section and a duty ratio of the drive pulses from the drive circuit.

12. The light source system according to claim 11, wherein the failure analysis section binarizes the output of the waveform conversion: section and obtains the duty ratio of the output of the waveform conversion section by counting high level periods and low level periods of a binarized waveform.

13. The light source system according to claim 11, comprising a display control section for displaying an analysis result of the failure analysis section.

14. The light source system according to claim 11, comprising a recording control section for recording an analysis result of the failure analysis section.

15. The light source system according to claim 1, wherein the illumination control section is provided at a processor section that performs image processing of an object image obtained by the endoscope.

* * * * *